United States Patent
Zhang et al.

(10) Patent No.: US 10,429,370 B2
(45) Date of Patent: Oct. 1, 2019

(54) DYNAMOELECTRIC MACHINE SEALING OIL MONITORING SYSTEM, COMPUTER PROGRAM PRODUCT AND RELATED METHODS

(71) Applicant: General Electric Company, Schenectady, NY (US)

(72) Inventors: Hua Zhang, Greer, SC (US); Jan Terry Stover, Easley, SC (US)

(73) Assignee: General Electric Company, Schenectady, NY (US)

( * ) Notice: Subject to any disclaimer, the term of this patent is extended or adjusted under 35 U.S.C. 154(b) by 344 days.

(21) Appl. No.: 15/596,543

(22) Filed: May 16, 2017

(65) Prior Publication Data

US 2018/0335416 A1   Nov. 22, 2018

(51) Int. Cl.
| | |
|---|---|
| G01N 33/28 | (2006.01) |
| G08B 21/18 | (2006.01) |
| H02K 9/24 | (2006.01) |
| G08B 25/10 | (2006.01) |
| G01F 1/00 | (2006.01) |

(52) U.S. Cl.
CPC ............ *G01N 33/28* (2013.01); *G08B 21/182* (2013.01); *G08B 25/10* (2013.01); *H02K 9/24* (2013.01); *G01F 1/00* (2013.01)

(58) Field of Classification Search
None
See application file for complete search history.

(56) References Cited

U.S. PATENT DOCUMENTS

| | | | | |
|---|---|---|---|---|
| 4,348,866 A | * | 9/1982 | Hayashida | ............... B60T 11/20 60/561 |
| 5,343,944 A | * | 9/1994 | Bassinger | ............... E21B 33/08 166/84.4 |
| 8,838,398 B2 | | 9/2014 | Andritz et al. | |
| 2010/0014791 A1 | * | 1/2010 | Versteegh | ............. F16C 19/184 384/147 |

(Continued)

OTHER PUBLICATIONS

Meltem Yildiz, Modeling and Simulation of Oil Leakage in Radial Lip Seals, Apr. 2010, 109 pages.*

(Continued)

*Primary Examiner* — Tung S Lau
(74) *Attorney, Agent, or Firm* — Dale Davis; Hoffman Warnick LLC

(57) ABSTRACT

Various embodiments of the disclosure include a system having: a computing device configured to monitor a sealing oil from a dynamoelectric machine by performing actions including: establish a baseline flow rate for the sealing oil through the dynamoelectric machine for designed operating conditions; calculate a plurality of average flow rates for the sealing oil through the dynamoelectric machine from a set of measured flow rates in each of a plurality of successive designated periods; provide an alert suggesting action in response to at least one of the average flow rates deviating from a threshold flow rate, the threshold flow rate derived from the baseline flow rate to indicate a fault in the sealing oil; and calculate an expected sealing life for the sealing oil based upon a pattern in the plurality of average flow rates for the plurality of successive designated periods.

20 Claims, 3 Drawing Sheets

(56) References Cited

U.S. PATENT DOCUMENTS

2011/0031068 A1* 2/2011 Henshaw ............. C10M 171/00
                                                    184/6.22
2011/0309780 A1  12/2011 Bandaru et al.
2012/0267168 A1* 10/2012 Grubb ................ B23K 26/0093
                                                    175/16
2013/0000919 A1*  1/2013 Linderman ............. E21B 41/04
                                                    166/344

OTHER PUBLICATIONS

Jahn Zuk in Dynamic Sealing Principles, Feb. 1976, 57 pages.*
Replacing Wet Seals with Dry Seals in Centrifugal Compressors, Oct. 2006, 8 pages.*
What determines seal leakage, May 2008, 3 pages.*
Determining The Life Of The Oil: How Do OEMs Calculate Oil Life Percentages, Oct. 2, 2018, 6 pages (Year: 2018).*

* cited by examiner

DYNAMOELECTRIC MACHINE SEALING OIL MONITORING SYSTEM, COMPUTER PROGRAM PRODUCT AND RELATED METHODS

FIELD OF THE INVENTION

The subject matter disclosed herein relates to dynamoelectric machines. More particularly, the subject matter disclosed herein relates to monitoring sealing oil in dynamoelectric machines, for example, generators or motors.

BACKGROUND OF THE INVENTION

Dynamoelectric machines, for example, generators and/or motors, use sealing oil to provide a barrier between an internally contained gas (e.g., hydrogen) and the ambient conditions. In the case of a hydrogen-sealed generator, the sealing oil forms a barrier between the hydrogen and the environment (ambient conditions), thereby retaining hydrogen within the generator. The sealing oil is kept at a slightly higher pressure than the hydrogen in order to prevent leakage of the hydrogen from the machine. When the sealing oil degrades in quality, it is prone to pressure drops, allowing the hydrogen to exit the generator, and the sealing oil to flow into the generator. This form of leakage can require a shutdown of the generator, along with connected power generation equipment (e.g., a turbomachine, motor, etc.), in order to perform maintenance and clean-up.

While many dynamoelectric machines are delivered and installed by a manufacturing and/or selling entity, these turbomachines are frequently managed (over their lifetime) by the customer that purchases the turbomachine. In order to ensure that the sealing oil in the dynamoelectric machine maintains a sufficient quality level to provide an effective seal, the customer conventionally draws a sample of the oil and sends it to a laboratory for testing. However, some customers improperly draw the oil samples, which can compromise accuracy of the testing. Others do not draw samples frequently enough to properly monitor the condition of the oil.

In other cases, sealing oil quality is estimated using empirical data that is tied to an expected lifetime of the oil based upon performance parameters of a dynamoelectric machine. In these cases, a dynamoelectric machine's monitoring system monitors the performance of the machine, e.g., operating speed, hours of operation, shutdown/startup events, etc., and based upon the performance of the machine, estimates a time at which the sealing oil will degrade in quality. These systems do not, however, test the sealing oil to determine its quality.

Due to the deficiencies in the above-noted techniques for monitoring seal oil quality, it is difficult to accurately assess the quality of seal oil in a dynamoelectric machine.

BRIEF DESCRIPTION OF THE INVENTION

Various embodiments of the disclosure include approaches for monitoring a sealing oil from a dynamoelectric machine. In some cases, a system includes: a computing device configured to monitor a sealing oil from a dynamoelectric machine by performing actions including: establish a baseline flow rate for the sealing oil through the dynamoelectric machine for designed operating conditions; calculate a plurality of average flow rates for the sealing oil through the dynamoelectric machine from a set of measured flow rates in each of a plurality of successive designated periods; provide an alert suggesting action in response to at least one of the average flow rates deviating from a threshold flow rate, the threshold flow rate derived from the baseline flow rate to indicate a fault in the sealing oil; and calculate an expected sealing life for the sealing oil based upon a pattern in the plurality of average flow rates for the plurality of successive designated periods.

Another aspect of the disclosure includes a computer program product having program code stored on a computer-readable medium, which when executed by at least one computing device, causes the at least one computing device to monitor a sealing oil from a dynamoelectric machine by performing actions including: establish a baseline flow rate for the sealing oil through the dynamoelectric machine for designed operating conditions; calculate a plurality of average flow rates for the sealing oil through the dynamoelectric machine from a set of measured flow rates in each of a plurality of successive designated periods; provide an alert suggesting action in response to at least one of the average flow rates deviating from a threshold flow rate, the threshold flow rate derived from the baseline flow rate to indicate a fault in the sealing oil; and calculate an expected sealing life for the sealing oil based upon a pattern in the plurality of average flow rates for the plurality of successive designated periods.

An additional aspect of the disclosure includes a computer-implemented method of monitoring a sealing oil from a dynamoelectric machine, performed on at least one computing device, the method including: establishing a baseline flow rate for the sealing oil through the dynamoelectric machine for designed operating conditions; calculating a plurality of average flow rates for the sealing oil through the dynamoelectric machine from a set of measured flow rates in each of a plurality of successive designated periods; providing an alert suggesting action in response to at least one of the average flow rates deviating from a threshold flow rate, the threshold flow rate derived from the baseline flow rate to indicate a fault in the sealing oil; and calculating an expected sealing life for the sealing oil based upon a pattern in the plurality of average flow rates for the plurality of successive designated periods.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
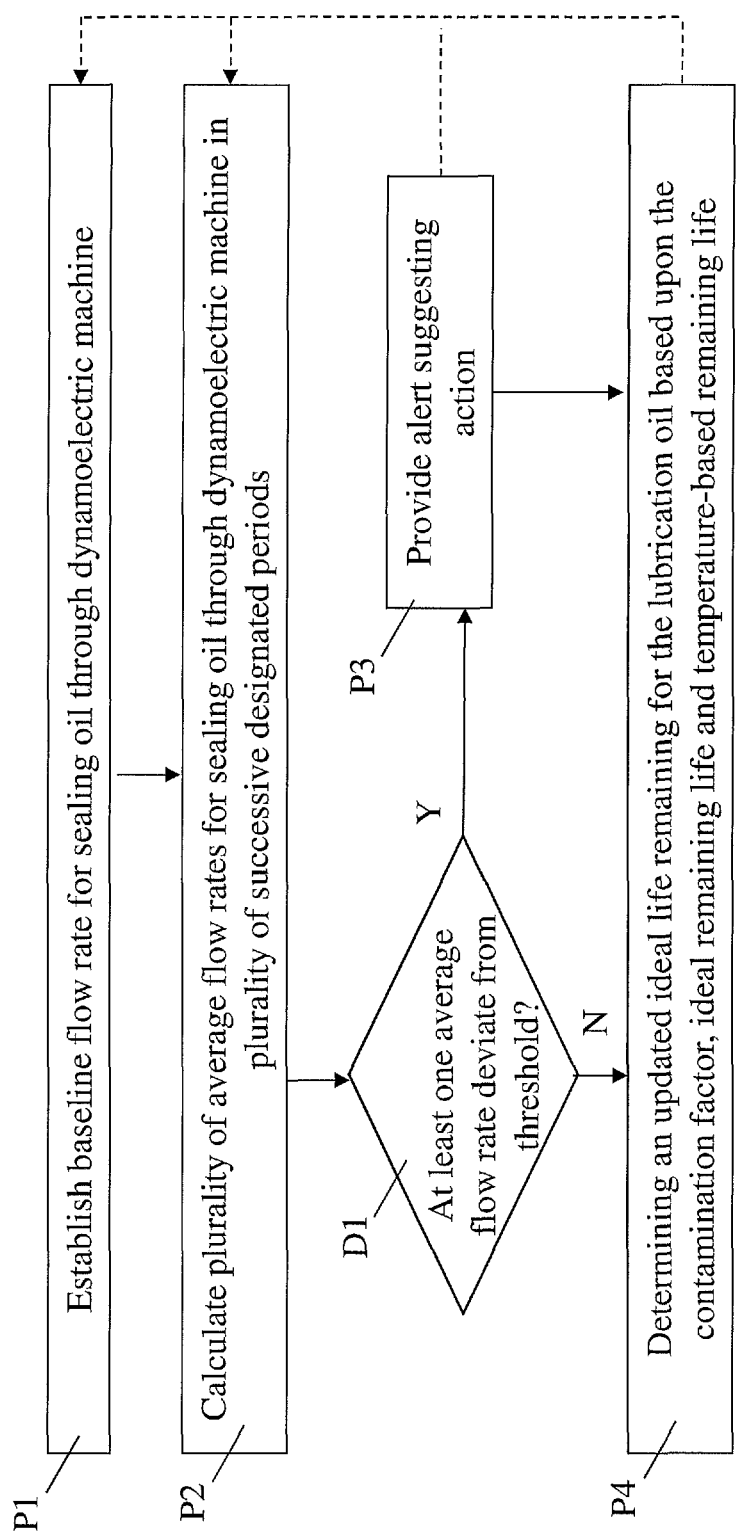
FIG. 1 shows a flow diagram illustrating processes in a method performed according to various embodiments of the invention.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the subject matter disclosed herein relates to sealing oil in dynamoelectric machines. More particularly, the subject matter disclosed herein relates to monitoring sealing oil in dynamoelectric machines, for example, hydrogen-sealed generators, using a flow-rate based approach.

As noted herein, it can be difficult to effectively monitor the quality of sealing oil in dynamoelectric machines, which can lead to undesirable degradation of the oil, and ultimately, damage the dynamoelectric machine that relies upon that oil for sealing.

In contrast to conventional approaches, various embodiments of the disclosure include systems, computer program products and associated methods to analyze a sealing oil using test data extracted from that oil. In various particular embodiments, approaches include continuously monitoring a flow rate of the sealing oil in order to predict a fault in that sealing oil. For example, some approaches include continuously measuring and averaging flow rates of the sealing oil in defined intervals, comparing those averages with a baseline flow rate for healthy sealing oil to detect a potential fault in the sealing oil, and/or predicting a future fault in the sealing oil based upon the continuously observed average flow rates.

In the following description, reference is made to the accompanying drawings that form a part thereof, and in which is shown by way of illustration specific embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Figure 2:
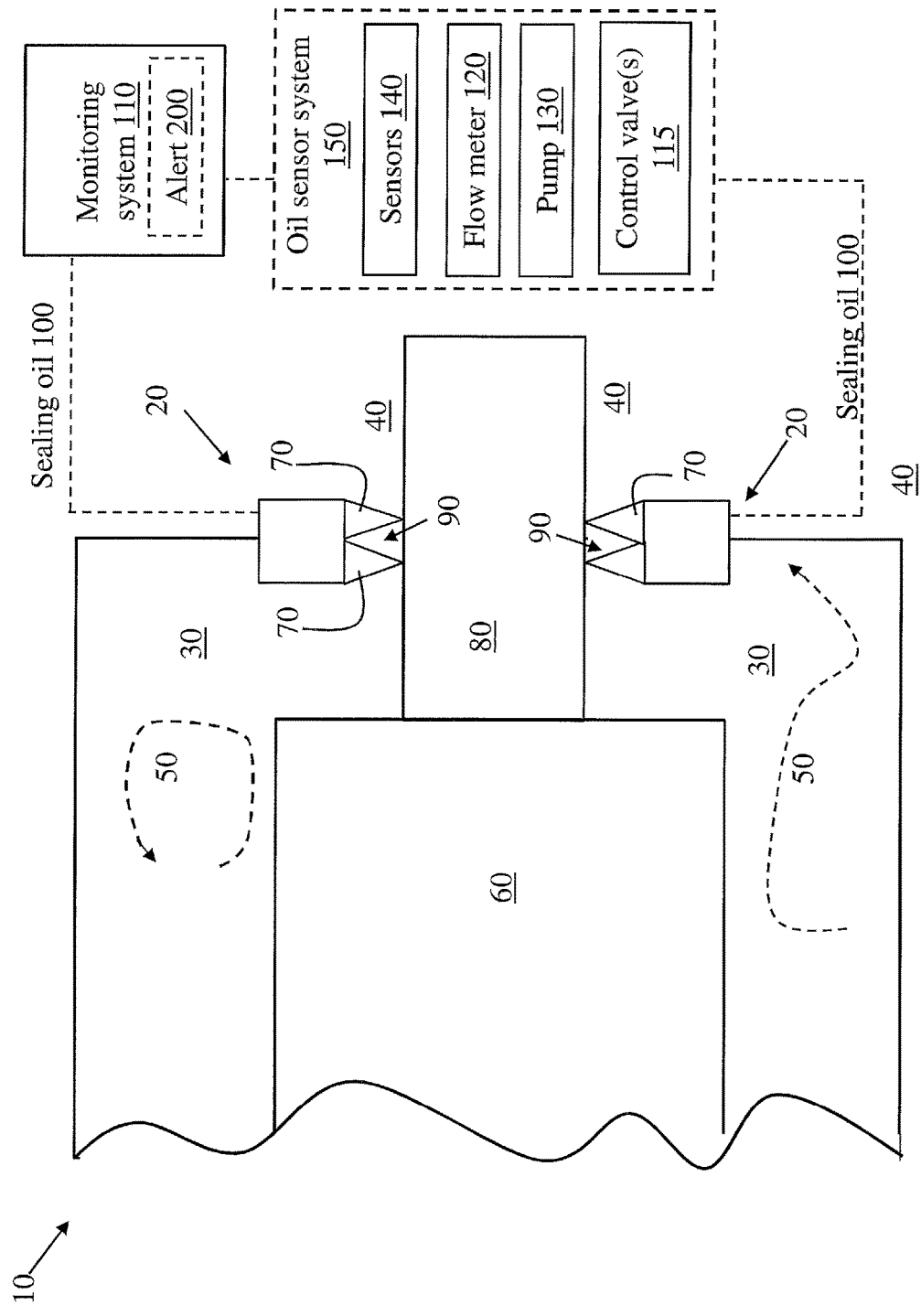
FIG. 2 shows a schematic cross-sectional depiction of a dynamoelectric machine and related monitoring system according embodiments of the invention.

FIG. 1 shows a flow diagram illustrating a process of monitoring a sealing oil (e.g., a sealing oil in a dynamoelectric machine such as a generator) according to various embodiments of the invention. FIG. 2 shows a schematic cross-sectional depiction of a portion of a dynamoelectric machine 10 (e.g., a generator) including a seal system 20 according to various embodiments of the disclosure. Seal system 20 can provide a seal between inner region 30 and ambient 40, e.g., to retain a cooling fluid 50 (arbitrary flow pattern shown as example within inner region 30). Cooling fluid 50 can include hydrogen in various embodiments, but may include other cooling fluids suitable for transferring heat away from dynamoelectric machine components 60, e.g., windings, bars, slots, etc. Seal system 20 can include a set of seals 70 surrounding shaft 80 of dynamoelectric machine 10, and a sealing oil slot 90 between seals 70 along shaft 80 for providing a fluid seal between inner region 30 and ambient 40. Sealing oil slot 90 can be at least partially filled with a sealing oil 100, (e.g., International Organization of Standards (ISO) viscosity grade (VG) VG 15, VG22, VG 32, or VG46, having a viscosity ranging from approximately 15 mm$^2$/s to 56 mm$^2$/s at 40° C. operation temperature), shown flowing into and out of seals 70 in a circuit. In various embodiments, a sealing oil monitoring system 110 (monitoring system) is coupled with dynamoelectric machine 10 to monitor sealing oil 100 as it moves into and out of dynamoelectric machine 10, and in particular, sealing oil slot 90. Monitoring system 110 can be coupled with one or more control valve(s) 115 for controlling flow of sealing oil 90 through sealing system 20. Monitoring system 110 can also be coupled with a flow meter 120 for measuring a flow rate of sealing oil 100 as it flows into and/or out of sealing oil slot 90 in dynamoelectric machine 10. In various embodiments, monitoring system 110 can also be coupled with a pump 130 for pumping sealing oil 100 through sealing oil slot 90.

Additionally, in various embodiments, one or more additional sensors 140 are coupled with dynamoelectric machine 10 and sealing oil monitoring system 110 for monitoring additional parameters of the dynamoelectric machine 10 and/or sealing oil 100. In some cases, additional sensors 140 can include one or more pressure gauges, temperature gauges and/or position sensors (e.g., for monitoring a position of one or more control valves 115). Additional sensors 140 can include electrical, electro-mechanical, or purely mechanical sensors conventional to sealing oil systems, e.g., piezo-electric sensors, optical sensors, infra-red (IR) sensors, hydraulic sensors, etc. Control valve(s) 115, flow meter 120, pump 130 and/or sensors 140 can be communicatively coupled with sealing oil monitoring system 110, e.g., via conventional wireless and/or hard-wired means, and can provide data about dynamoelectric machine 10 and sealing oil 100 on a periodic, on-demand, scheduled, or other basis. In some cases, one or more of control valve(s) 115, flow meter 120, pump 130 and/or sensors 140 can be housed or otherwise contained within an oil sensor system 150, as described herein, however, in other cases, one or more of these components may be independently coupled with seal system 20 and monitoring system 110.

Returning to FIG. 1 (with continuing reference to FIG. 2), processes of monitoring sealing oil 100 as described herein can be performed, e.g., by at least one computing device, as described herein. In other cases, these processes can be performed according to a computer-implemented method of monitoring a sealing oil. In still other embodiments, these processes can be performed by executing computer program code on at least one computing device, causing the at least one computing device to monitor a sealing oil. In general, the process can include the following sub-processes:

Process P1: monitoring system 100 establishes a baseline flow rate ($Q_0$) for sealing oil 100 through dynamoelectric machine 10 for designed operating conditions. In various embodiments, the baseline flow rate ($Q_0$) can be established according to a rated flow rate for the particular model of dynamoelectric machine 10, e.g., from the manufacturer of dynamoelectric machine 10, or from a standard set according to an industry governing body. In some cases, baseline flow rate ($Q_0$) can be established over a period of operation of dynamoelectric machine 10 at a designed operating condition, e.g., a designed output range of dynamoelectric machine 10. For example, in some cases, dynamoelectric machine 10 may be designed and rated (e.g., by its manufacturer or a governing body) to operate between X megawatts (MW) and X+Y MW, and baseline flow rate ($Q_0$) can be a flow rate measured by flow meter 120 across the operating range. This flow rate can include an average flow rate, or other statistically significant sampling of flow rates for sealing oil 100 within the designed operating range of dynamoelectric machine 10.

Process P2: monitoring system 100 calculates a plurality of average flow rates ($Q_{ave}$) for sealing oil 100 through dynamoelectric machine 10 from a set of measured flow rates (Q) in each of a plurality of successive designated periods ($T_0$). In some cases, flow rates (Q) are measured continuously by flow meter 120, or are polled from flow meter 120 by sealing oil monitoring system 110 on a periodic or continuous basis. In various embodiments, sealing oil monitoring system 110 continuously gathers data about measured flow rates (Q) from flow meter 120 during successive periods of time. In some cases, the successive periods are separate, successive periods, of between approximately (+/−1-3 percent) one minute and approximately five minutes. Sealing oil monitoring system 110 can calculate the average flow rates ($Q_{ave}$) for each of the successive, separate periods on a rolling basis (e.g., as each measurement is obtained), or on a periodic or semi-periodic basis (e.g., at the end of each successive period, or at any interval within each period). According to various embodiments, each average flow rate ($Q_{ave}$) is calculated according to:

$$Q_{ave} = \frac{1}{T_0} \int_0^{T_0} Q(t) * dt \qquad \text{(Equation 1)}$$

Where: $T_0$ equals the time for each successive period.

Process P3: monitoring system 100 provides an alert 200 suggesting action in response to at least one of the average flow rates ($Q_{ave}$) deviating from a threshold flow rate ($Q_T$) (result of Yes to decision D1). In various embodiments, threshold flow rate ($Q_T$) is derived from baseline flow rate ($Q_0$) to indicate a fault in sealing oil 100. In some cases, threshold flow rate ($Q_T$) can be equal to baseline flow rate ($Q_0$). In various other embodiments, threshold flow rate ($Q_T$) includes a range of flow rates, which can include a statistical variation from baseline flow rate ($Q_0$). That is, the threshold flow rate ($Q_T$) can range from a low value to a high value, each of which represents a statistical variation, such as a percentage of flow rate (Q) values distributed within a statistical distribution (e.g., three standard deviations) of baseline flow rate ($Q_0$). In some cases, the standard deviation, $\sigma_Q$, is about 0.3% of $Q_0$. An alert 200 can include any visual, audio, tactile or other detectable indicator demonstrating that one or more average flow rate(s) ($Q_{ave}$) deviate from threshold flow rate ($Q_T$). Alert 200 can be provided to a user, e.g., via a user interface (UI) or other suitable communication mechanism, as further discussed with respect to environment 301 in FIG. 3. According to various embodiments, calculating whether to provide an alert 200 suggesting action based upon average flow rate ($Q_{ave}$) with respect to threshold flow rate ($Q_T$) can be performed according to:

$$Q_T < |Q_{ave} - Q_0| \qquad \text{(Equation 2)}$$

Where $Q_T = Q_0 * T_m$, where $T_m$ is a threshold multiplier. In various embodiments, threshold multiplier ($T_m$) is equal to a fraction less than 1.0, e.g., 0.1-0.9 (with any number of decimal places possible). As is understood from Equation 2, where the difference in $Q_{ave}$ and $Q_0$ (in absolute value) is greater than $Q_T$, an alert 200 to take action is provided, e.g., to check sealing oil 100 or related pump 130. In some particular cases, where the following equation is satisfied, an alert 200 to take action will be provided:

$$\frac{|Q_{ave} - Q_0|}{Q_0} > 0.1 \qquad \text{(Equation 3)}$$

In other embodiments, a difference between $Q_{ave}$ and $Q_0$ can indicate a particular type of issue with sealing oil 100, e.g., where the difference between $Q_{ave}$ and $Q_0$ is greater than zero, an erosion issue is probable, or where the difference between $Q_{ave}$ and $Q_0$ is less than zero, a coking issue is probable.

Process P4: monitoring system 100 calculates an expected sealing life for sealing oil 100 based upon a pattern in the plurality of average flow rates ($Q_{ave}$) for the plurality of successive designated periods (No to Decision D1). In various embodiments, sealing oil monitoring system 110 is configured to provide an expected failure alert (e.g., alert 200) prior to expiration of the expected sealing life, e.g., at one or more intervals prior to the expiration in order to allow a user or other system to address the issue causing the expected failure. In various embodiments the pattern in average flow rates ($Q_{ave}$) includes a trend in the average flow rates ($Q_{ave}$) moving relative to threshold flow rate ($Q_T$), e.g., approaching, moving away from, or varying with respect to $Q_T$. In some cases, the expected sealing life (LES) is the difference between the current time ($t_i$) and the expected failure time ($t_f$), in equation form:

$$LES = t_f - t_i \qquad \text{(Equation 4)}$$

In various embodiments, the pattern in average flow rates ($Q_{ave}$) can be calculated according to:

$$K_2 = K_0 + w_1 * t + w_2 * t^2 \qquad \text{(Equation 5)}$$

Where $K_0$ is an oil flow resistance calculated at control valve 115 proximate commissioning of dynamoelectric machine 10, $K_2$ is the oil flow resistance at a given time (t) of measurement, and w1 and w2 are parameters dynamically updated with calculated average flow rates ($Q_{ave}$) at each designated period, where the weight factors of $w_1$ and $w_2$, are capturing the impact of operation time to contamination of seal system 20 including degradation of sealing oil 100. The flow resistance of seal system 20 generally increases with increasing operation time, with a correlation of linear component $w_1$, and quadratic component of $w_2$. That is, at given time (t), if the absolute value of $K_2 - K_0 > X$, sealing oil monitoring system 110 will schedule maintenance at that time (t), which is equivalent to time of failure ($t_f$). In some cases, X can be equal to the threshold multiplier ($T_m$), however, in other cases, X can be independent of threshold multiplier ($T_m$). In one example, X can be equal to 0.05 to 0.15, with a particular example of X=0.1.

In various embodiments, Processes P1-P4 can be iterated (repeated) periodically (e.g., according to schedule of x times per y period, and/or continuously) in order to monitor the health of sealing oil 100. In some cases, processes P2-P4 (including Decision D1) can be repeated, for example, by obtaining new sample(s) of the sealing oil 100 and performing associated processes described herein. In these cases, process P1 may not need to be repeated because the baseline value(s) may be substantially unchanged between some testing intervals.

In some cases, additional modelling equations may aid in understanding the various embodiments of the disclosure. The following modelling equations are examples of approaches for calculating particular parameters, and are meant merely to be illustrative.

Control valve 115 flow coefficient ($C_v$):

$$C_v : a * [\text{valve open position}^3 + b * \text{valve open position}^2 - c * \text{valve open position} + d] \qquad \text{(Equation 6)}$$

Where the valve open position is equal to the degree position reading of control valve 115, and a, b, c and d are equal to constants for a particular model of control valve 115 (e.g., a=0.0161, b=0.2965, c=1.105, d=0.8971).

Viscosity ($\mu$) of sealing oil 100:

$$\frac{\mu}{\mu_0} = 8256.9 * T_{oil}^{-1.822} \qquad \text{(Equation 7)}$$

Where $T_{oil}$ is the temperature reading of sealing oil 100, where constant 8.256.9 is particular to the model of temperature sensor, $\mu$ is the actual (measured) lubrication oil viscosity, and $\mu_0$ is a reference lubrication oil viscosity. This mathematical operation can be used to calculate viscosity at temperature T, using a reference temperature $T_0$ from a known value of $\mu_0$.

Flow rate (Q) of sealing oil 100:

$$Q = \frac{\mu}{\mu_0} * C_V * \sqrt{\Delta P} * \frac{1}{G} \quad \text{(Equation 8)}$$

Where ΔP is pressure differential across control valve 115 and G is specific gravity of sealing oil 100, e.g., 0.85.

Sealing oil 100 flow resistance model:

$$Q = K_2 \sqrt{P_{oil}} \quad \text{(Equation 9)}$$

Where $K_2$ is the flow resistance of sealing oil 100 across control valve 115 and $P_{oil}$, is the seal oil 100 pressure, as measured by the pressure sensor (sensors 140).

It is understood that in the flow diagrams shown and described herein, other processes may be performed while not being shown, and the order of processes can be rearranged according to various embodiments. Additionally, intermediate processes may be performed between one or more described processes. The flow of processes shown and described herein is not to be construed as limiting of the various embodiments.

Figure 3:
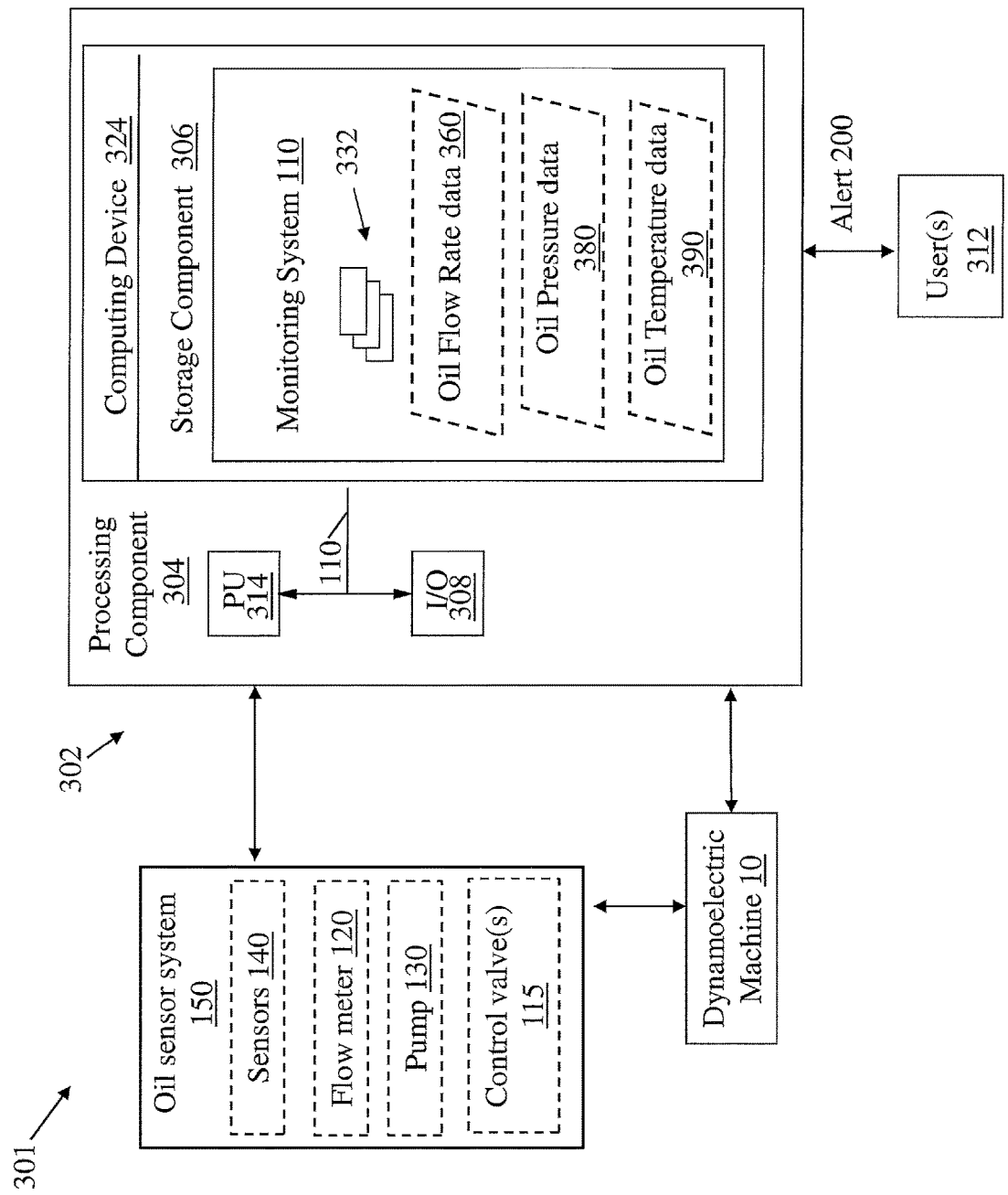
FIG. 3 shows an environment including a system according to various embodiments of the invention.

FIG. 3 shows an illustrative environment 301 including sealing oil monitoring system 110, for performing the functions described herein according to various embodiments of the invention. To this extent, the environment 301 includes a computer system 302 that can perform one or more processes described herein in order to monitor a sealing oil, e.g., from a dynamoelectric machine 10. In particular, the computer system 302 is shown as including monitoring system 110, which makes computer system 302 operable to monitor a sealing oil 100 by performing any/all of the processes described herein and implementing any/all of the embodiments described herein.

The computer system 302 is shown including a computing device 324, which can include a processing component 304 (e.g., one or more processors), a storage component 306 (e.g., a storage hierarchy), an input/output (I/O) component 308 (e.g., one or more I/O interfaces and/or devices), and a communications pathway 310. In general, the processing component 304 executes program code, such as the monitoring system 110, which is at least partially fixed in the storage component 306. While executing program code, the processing component 304 can process data, which can result in reading and/or writing transformed data from/to the storage component 306 and/or the I/O component 308 for further processing. The pathway 310 provides a communications link between each of the components in the computer system 302. The I/O component 308 can comprise one or more human I/O devices, which enable a user (e.g., a human and/or computerized user) 312 to interact with the computer system 302 and/or one or more communications devices to enable the system user 312 to communicate with the computer system 302 using any type of communications link. To this extent, the monitoring system 110 can manage a set of interfaces (e.g., graphical user interface(s), application program interface, etc.) that enable human and/or system users 312 to interact with the monitoring system 110. Further, the monitoring system 110 can manage (e.g., store, retrieve, create, manipulate, organize, present, etc.) data, such as oil flow rate data 360 (e.g., data about the flow rate of the oil, obtained by flow meter 120), oil temperature data 380 (e.g., data about the temperature of the oil, obtained by sensors 140) and/or oil pressure data 390 (e.g., data about the pressure measurement of the oil, as obtained by sensors 140) using any solution. The monitoring system 110 can additionally communicate with dynamoelectric machine 10 and/or an oil sensor system 150 (including, in some cases, sensors 140, flow meter 120, pump 130 and/or control valves 115) via wireless and/or hardwired means.

In any event, the computer system 302 can comprise one or more general purpose computing articles of manufacture (e.g., computing devices) capable of executing program code, such as the monitoring system 110, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the monitoring system 110 can be embodied as any combination of system software and/or application software. It is further understood that the monitoring system 110 can be implemented in a cloud-based computing environment, where one or more processes are performed at distinct computing devices (e.g., a plurality of computing devices 324), where one or more of those distinct computing devices may contain only some of the components shown and described with respect to the computing device 324 of FIG. 3.

Further, the monitoring system 110 can be implemented using a set of modules 332. In this case, a module 332 can enable the computer system 302 to perform a set of tasks used by the monitoring system 110, and can be separately developed and/or implemented apart from other portions of the monitoring system 110. As used herein, the term "component" means any configuration of hardware, with or without software, which implements the functionality described in conjunction therewith using any solution, while the term "module" means program code that enables the computer system 302 to implement the functionality described in conjunction therewith using any solution. When fixed in a storage component 306 of a computer system 302 that includes a processing component 304, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 302.

When the computer system 302 comprises multiple computing devices, each computing device may have only a portion of monitoring system 110 fixed thereon (e.g., one or more modules 332). However, it is understood that the computer system 302 and monitoring system 110 are only representative of various possible equivalent computer systems that may perform a process described herein. To this extent, in other embodiments, the functionality provided by the computer system 302 and monitoring system 110 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 302 includes multiple computing devices 324, the computing devices can communicate over any type of communications link. Further, while performing a process described herein, the computer system 302 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 302 can obtain or provide data, such as oil flow rate data 360, oil pressure data 380 and/or oil temperature data 390 using any solution. The computer system 302 can generate oil flow rate data 360, oil pressure data 380 and/or oil temperature data 390, from one or more data stores, receive oil flow rate data 360, oil pressure data 380 and/or oil temperature data 390, from another system such as the oil sensor system 150 and/or the user 312, send oil flow rate data 360, oil pressure data 380 and/or oil temperature data 390 to another system, etc.

While shown and described herein as a method and system for monitoring a sealing oil, it is understood that aspects of the invention further provide various alternative embodiments. For example, in one embodiment, the invention provides a computer program fixed in at least one computer-readable medium, which when executed, enables a computer system to monitor a sealing oil. To this extent, the computer-readable medium includes program code, such as the monitoring system 110 (FIG. 2, FIG. 3), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the monitoring system 110 (FIG. 2, FIG. 3), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of monitoring a sealing oil. In this case, a computer system, such as the computer system 302 (FIG. 3), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the various embodiments of the invention, including, e.g., the monitoring system 110, is to monitor a sealing oil, e.g., a sealing oil 100 from a dynamoelectric machine (e.g., dynamoelectric machine 10). It is understood that the monitoring system 110 could be implemented monitor a sealing oil in a plurality of distinct applications, e.g., to monitor sealing oil in an automobile system, to monitor lubrication oil in a piece of heavy machinery, etc.

Various additional embodiments can include a sealing oil monitoring apparatus 500 (FIGS. 4 and 5), coupled with dynamoelectric machine 10, which can include one or more components of the monitoring system 110 (and associated functionality), along with the oil sensor system 150. The sealing oil monitoring apparatus can be configured to non-invasively monitor one or more condition(s) of the sealing oil. In some cases, the sealing oil monitoring apparatus (and in particular, the oil sensor system 150) can monitor one or more parameters of the sealing oil, including but not limited to: an International Organization of Standards (ISO) particle count, a ferrous material particle count, a water content and/or a chemical breakdown.

In various embodiments, sealing oil monitoring apparatus 500 can continuously monitor these parameters, and compare these parameters with acceptable thresholds (e.g., levels or ranges) to determine whether the sealing oil is at a desired level. The sealing oil monitoring apparatus can include an interface, e.g., a human-machine interface (HMI) for providing one or more alerts when the determined parameter(s) of the sealing oil deviate, approach, and/or trend toward an unacceptable threshold/range.

In some cases, sealing oil monitoring apparatus 500 can be mounted or otherwise coupled with dynamoelectric machine 10. In other cases, sealing oil monitoring apparatus 500 is located proximate dynamoelectric machine 10 to provide real-time monitoring of the condition of the sealing oil.

In various embodiments, sealing oil monitoring apparatus 500 can be fluidly connected with the existing sealing oil reservoir in the dynamoelectric machine. In some particular embodiments, sealing oil monitoring apparatus 500 is fluidly connected with the return line drain section of the oil reservoir. In some cases, sealing oil monitoring apparatus 500 includes an oil supply line for extracting oil from the reservoir, and a drain line for draining tested oil back to the reservoir. The apparatus 500 can also include a mount for mounting onto the reservoir or a proximate portion of dynamoelectric machine 10.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
   at least one computing device configured to monitor a sealing oil from a dynamoelectric machine by performing actions including:
      establish a baseline flow rate for the sealing oil through the dynamoelectric machine for designed operating conditions;
      calculate a plurality of average flow rates for the sealing oil through the dynamoelectric machine from a set of measured flow rates in each of a plurality of successive designated periods;
      provide an alert suggesting action in response to at least one of the average flow rates deviating from a threshold flow rate, the threshold flow rate derived from the baseline flow rate to indicate a fault in the sealing oil; and
      calculate an expected sealing life for the sealing oil based upon a pattern in the plurality of average flow rates for the plurality of successive designated periods.

2. The system of claim 1, wherein the at least one computing device is further configured to provide an expected failure alert prior to expiration of the expected sealing life.

3. The system of claim 1, wherein the threshold flow rate includes a range of flow rates.

4. The system of claim 3, wherein the range of flow rates includes a statistical variation from the baseline flow rate.

5. The system of claim 1, wherein the pattern includes a trend in the plurality of average flow rates moving relative to the threshold flow rate.

6. The system of claim 1, wherein the designed operating conditions include a range of rated operating conditions for the dynamoelectric machine.

7. The system of claim 1, wherein the dynamoelectric machine includes a hydrogen-cooled generator.

8. The system of claim 7, further comprising a flow meter fluidly coupled with the sealing oil in the dynamoelectric machine, the flow meter providing readings of the plurality of measured flow rates.

9. The system of claim 1, wherein the successive designated periods include separate successive periods of between approximately one minute and approximately five minutes.

10. A computer program product comprising program code stored on a non-transitory computer-readable medium, which when executed by at least one computing device, causes the at least one computing device to monitor a sealing oil from a dynamoelectric machine by performing actions including:
    establish a baseline flow rate for the sealing oil through the dynamoelectric machine for designed operating conditions;
    calculate a plurality of average flow rates for the sealing oil through the dynamoelectric machine from a set of measured flow rates in each of a plurality of successive designated periods;
    provide an alert suggesting action in response to at least one of the average flow rates deviating from a threshold flow rate, the threshold flow rate derived from the baseline flow rate to indicate a fault in the sealing oil; and
    calculate an expected sealing life for the sealing oil based upon a pattern in the plurality of average flow rates for the plurality of successive designated periods.

11. The computer program product of claim 10, wherein the program code causes the at least one computing device to further provide an expected failure alert prior to expiration of the expected sealing life.

12. The computer program product of claim 10, wherein the threshold flow rate includes a range of flow rates, wherein the range of flow rates includes a statistical variation from the baseline flow rate.

13. The computer program product of claim 10, wherein the pattern includes a trend in the plurality of average flow rates moving relative to the threshold flow rate.

14. The computer program product of claim 10, wherein the designed operating conditions include a range of rated operating conditions for the dynamoelectric machine.

15. The computer program product of claim 10, wherein the successive designated periods include separate successive periods of between approximately one minute and approximately five minutes.

16. A computer-implemented method of monitoring a sealing oil from a dynamoelectric machine, performed on at least one computing device, the method comprising:
    establishing a baseline flow rate for the sealing oil through the dynamoelectric machine for designed operating conditions;
    calculating a plurality of average flow rates for the sealing oil through the dynamoelectric machine from a set of measured flow rates in each of a plurality of successive designated periods;
    providing an alert suggesting action in response to at least one of the average flow rates deviating from a threshold flow rate, the threshold flow rate derived from the baseline flow rate to indicate a fault in the sealing oil; and
    calculating an expected sealing life for the sealing oil based upon a pattern in the plurality of average flow rates for the plurality of successive designated periods.

17. The method of claim 16, further comprising providing an expected failure alert prior to expiration of the expected sealing life.

18. The method of claim 16, wherein the threshold flow rate includes a range of flow rates, wherein the range of flow rates includes a statistical variation from the baseline flow rate.

19. The method of claim 16, wherein the pattern includes a trend in the plurality of average flow rates moving relative to the threshold flow rate.

20. The method of claim 16, wherein the successive designated periods include separate successive periods of between approximately one minute and approximately five minutes.

* * * * *